United States Patent
Chen et al.

(10) Patent No.: US 10,114,024 B2
(45) Date of Patent: Oct. 30, 2018

(54) BIOMOLECULE-GRAPHENE QUANTUM DOT CONJUGATES AND USE THEREOF

(71) Applicant: Nanyang Technological University, Singapore (SG)

(72) Inventors: Peng Chen, Singapore (SG); Xin Ting Zheng, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 14/471,928

(22) Filed: Aug. 28, 2014

(65) Prior Publication Data
US 2015/0064720 A1  Mar. 5, 2015

Related U.S. Application Data

(60) Provisional application No. 61/871,007, filed on Aug. 28, 2013.

(51) Int. Cl.
G01N 33/58 (2006.01)
G01N 21/64 (2006.01)

(52) U.S. Cl.
CPC ......... *G01N 33/588* (2013.01); *G01N 21/648* (2013.01); *G01N 21/6458* (2013.01); *G01N 2021/6439* (2013.01)

(58) Field of Classification Search
CPC .......................... G01N 33/5005; G01N 33/588
See application file for complete search history.

(56) References Cited

PUBLICATIONS

Yang et al., "Sensitive electrochemical immunosensor for the detection of cancer biomarker using quantum dot functionalized graphene sheets as labels", Sensors and Actuators B, vol. 155, pp. 357-360, published Dec. 2, 2010.*
Gao et al., Covalent Immobilization of Proteins on Carbon Nanotubes Using the Cross-Linker 1-Ethyl-3-(3-dimethylaminopropyl)carbodiimide-a Critical Assessment, Bioconjugate Chem. vol. 19, No. 10, pp. 1945-1950, published Aug. 29, 2008.*
Zhou et al., "Reducing Graphene Oxide via Hydroxylamine: A Simple and Efficient Route to Graphene", J. Phys. Chem., vol. 115, p. 11957-11961, published Jun. 2, 2011.*
Xing et al., "DNA aptamer functionalized nanomaterials for intracellular analysis, cancer cell imaging and drug delivery", Sciencedirect, vol. 16, pp. 429-435, published Apr. 26, 2012.*
Liang et al., "Molecular Dynamics Simulation on Graphene", Chin. J. Chem. Phys., vol. 22, No. 6, pp. 627-634, published Dec. 27, 2009.*
Shen et al., "Covalent attaching protein to graphene oxide via diimide-activated amidation", Colloids and Surfaces B: Biointerfaces, vol. 81, pp. 434-438, published Jul. 22, 2010.*
Roy et al. "Graphene oxide for electrochemical sensing application", J. Mater. Chem. vol. 21, pp. 14725-14731, published Aug. 16, 2011.*

(Continued)

*Primary Examiner* — Tracy Vivlemore
*Assistant Examiner* — Nam P Nguyen
(74) *Attorney, Agent, or Firm* — Seed IP Law Group LLP

(57) ABSTRACT

The invention relates to biomolecules conjugated to graphene quantum dots, and in particular, to use of such biomolecule-graphene quantum dot conjugates as fluorophores for imaging applications.

11 Claims, 7 Drawing Sheets

(56) References Cited

PUBLICATIONS

Castan-laurell et al., "Apelin, a promising target for type 2 diabetes treatment?" *Trends in Endocrinology and Metabolism* 23(5):234-241, May 2012.
Cui et al., "One at a time, live tracking of NGF axonal transport using quantum dots," *PNAS* 104(34):13666-13671, Aug. 21, 2007.
Dong et al., "Blue luminescent graphene quantum dots and graphene oxide prepared by tuning the carbonization degree of citric acid," *Carbon* 50:4738-4743, 2012.
Dong et al., "One-step and high yield simultaneous preparation of single- and multi-layer graphene quantum dots from CX-72 carbon black," *J. Mater. Chem.* 22:8764-8766, 2012.
Gao et al., "New insights into the structure and reduction of graphite oxide," *Nature Chemistry* 1:403-408, Aug. 2009.
Giudice et al., "Differential endocytosis and signaling dynamics of insulin receptor variants IR-A and IR-B," *J. Cell Sci.* 124:801-811, 2012.
Hotamisligil et al., "IRS-1-Mediated Inhibition of Insulin Receptor Tyrosine Kinase Activity in TNF-$\alpha$-and Obesity-Induced Insulin Resistance," *Science* 271:665-668, Feb. 2, 1996.
Inokuchi, "Membrane microdomains and insulin resistance," *FEBS Letters* 584:1864-1871, 2010.
Jiang et al., "Labeling and Tracking P2 Purinergic Receptors in Living Cells Using ATP-Conjugated Quantum Dots," *Adv. Funct. Mater.* 21:2776-2780, 2011.
Jin et al., "Tuning the Photoluminescence of Graphene Quantum Dots through the Charge Transfer Effect of Functional Groups," *ACS Nano* 7(2):1239-1245, 2013.
Lin et al., "Creating high yield water soluble luminescent graphene quantum dots via exfoliating and disintegrating carbon nanotubes and graphite flakes," *Chem Commun.* 48:10177-10179, 2012.
Liu et al., "Glutathione-functionalized graphene quantum dots as selective fluorescent probes for phosphate-containing metabolites," *Nanoscale* 5:1810-1815, 2013.
Liu et al., "PEGylated Nanographene Oxide for Delivery of Water-Insoluble Cancer Drugs." *J. Am. Chem. Soc.* 130:10876-10877, 2008.
Lukinavičius et al., "A near-infrared fluorophore for live-cell super-resolution microscopy of cellular proteins," *Nature Chemistry* 5:132-139, Feb. 2013.
Marshall, "Kinetics of Insulin Receptor Internalization and Recycling in Adipocytes," *The Journal of Biological Chemistry* 260(7):4136-4144, 1985.
Michalet et al., "Quantum Dots for Live Cells, in Vivo Imaging, and Diagnostics," *Science* 307:538-544, Jan. 28, 2005.
Pan et al., "Cutting $sp^2$ clusters in graphene sheets into colloidal graphene quantum dots with strong green fluorescence," *J. Mater. Chem.* 22:3314-3318, 2012.
Pan et al., "Hydrothermal Route for Cutting Graphene Sheets into Blue-Luminescent Graphene Quantum Dots," *Adv. Mater.* 22:734-738, 2010.
Pandini et al., "Insulin/Insulin-like Growth Factor I Hybrid Receptors Have Different Biological Characteristics Depending on the Insulin Receptor Isoform Involved," *The Journal of Biological Chemistry* 277(42):39684-39695, 2002.
Peng et al., "Graphene Quantum Dots Derived from Carbon Fibers," *Nano Lett.* 12:844-849, 2012.
Pinaud et al., "Probing cellular events, one quantum dot at a time," *Nature Methods* 7(4):275-285, Apr. 2010.
Rajan et al., "Ligand-Bound Quantum Dot Probes for Studying the Molecular Scale Dynamics of Receptor Endocytic Trafficking in Live Cells," *ACS Nano* 2(6):1153-1166, 2008.
Resch-Genger et al., "Quantum dots versus organic dyes as fluorescent labels," *Nature Methods* 5(9):763-775, Sep. 2008.
Saltiel et al., "Insulin signalling and the regulation of glucose and lipid metabolism," *Nature* 414:799-806, Dec. 13, 2001.
Shen et al., "Graphene quantum dots: emergent nanolights for bioimaging, sensors, catalysis and photovoltaic devices," *Chem. Commun* 48:3686-3699, 2012.
Sun et al., "Improvement of Photoluminescence of Graphene Quantum Dots with a Biocompatible Photochemical Reduction Pathway and Its Bioimaging Application," *ACS Appl. Mater. Interfaces* 5:1174-1179, 2013.
Sun et al., "Nano-Graphene Oxide for Cellular Imaging and Drug Delivery," *Nano Res* 1:203-212, 2008.
Tang et al., "Deep Ultraviolet Photoluminescence of Water-Soluble Self-Passivated Graphene Quantum Dots," *ACS Nano* 6(6):5102-5110, 2012.
Tetsuka et al., "Optically Tunable Amino-Functionalized Graphene Quantum Dots," *Adv. Mater* 24:5333-5338, 2012.
Than et al., "Apelin inhibits adipogenesis and lipolysis through distinct molecular pathways," *Molecular and Cellular Endocrinology* 362:227-241, 2012.
Trischitta et al., "Evidence of a defect in insulin-receptor recycling in adipocytes from older rats," *Am J Physiol* 254(1):E39-E44, 1988.
Vu et al., "Peptide-Conjugated Quantum Dots Activate Neuronal Receptors and Initiate Downstream Signaling of Neurite Growth," *Nano Letters* 5(4):603-607, 2005.
Yan et al., "Colloidal Graphene Quantum Dots with Well-Defined Structures," *Accounts of Chemical Research* 46(10):2254-2262, 2013.
Zhang et al., "Creating New Fluorescent Probes for Cell Biology," *Nat. Rev. Mol. Cell. Biol.* 3(12):906-918, 2002.
Zhang et al., "Graphene quantum dots: an emerging material for energy-related applications and beyond," *Energy Environ. Sci.* 5:8869-8890, 2012.
Zhang et al., "Roles of Cholesterol in Vesicle Fusion and Motion," *Biophysical Journal* 97:1371-1380, Sep. 2009.
Zhu et al., "Apelin stimulates glucose uptake through the PI3K/Akt pathway and improves insulin resistance in 3T3-L1 adipocytes," *Mol. Cell Biochem* 353:305-313, 2011.
Zhu et al., "Graphene quantum dots with controllable surface oxidation, tunable fluorescence and up-conversion emission," *RSC Advances* 2(7):2717-2720, 2012.
Zhu et al., "Strongly green-photoluminescent graphene quantum dots for bioimaging applications," *Chem. Commun.* 47(24):6858-6860, 2011.
Zhu et al., "Surface Chemistry Routes to Modulate the Photoluminescence of Graphene Quantum Dots: From Fluorescence Mechanism to Up-Conversion Bioimaging Applications," *Adv. Funct. Mater.* 22:4732-4740, 2012.
Zhuo et al., "Upconversion and Downconversion Fluorescent Graphene Quantum Dots: Ultrasonic Preparation and Photocatalysis," *ACS Nano* 6(2):1059-1064, 2012.
Zou et al., "Role of adipocytokines in obesity-associated insulin resistance," *Journal of Nutritional Biochemistry* 19:277-286, 2008.

* cited by examiner

BIOMOLECULE-GRAPHENE QUANTUM DOT CONJUGATES AND USE THEREOF

CROSS-REFERENCE TO RELATED APPLICATION

This application claims the benefit of priority of U.S. Provisional Patent Application No. 61/871,007, filed Aug. 28, 2013, the contents of which are hereby incorporated by reference in its entirety for all purposes.

BACKGROUND

Technical Field

The invention relates to biomolecules conjugated to graphene quantum dots, and in particular, to use of such biomolecule-graphene quantum dot conjugates as a fluorophore for imaging methods.

Description of the Related Art

Real-time tracking of fluorophore-tagged biomolecules is instrumental to reveal the dynamic cell functions at single cell or sub-cellular level. An ideal fluorophore should be conveniently excitable, bright, stable, equipped with chemical handles for readily conjugation with target molecules, biocompatible, and small enough to minimize physical hindrance.

Currently, organic dyes and fluorescent proteins are predominantly used for bio-imaging. They, however, intrinsically suffer from poor photo-stability problem which makes long-term imaging challenging because of fast photobleaching. In addition, labeling with fluorescent proteins involves non-trivial molecular biology processes including construction of chimeric plasmids and subsequent transfection in live cells. And the abundance of expressed chimeric fluorescent proteins is often low due to ineffective hijacking of the native genetic machinery and the damages or cytotoxicity caused by the transfection procedure.

Semiconductor quantum dots (QDs) have been regarded as the promising alternative to organic fluorophores because of their high brightness and photo-stability. They have been successfully employed for live-imaging of various cellular processes. But QDs are toxic due to leaching of heavy metal ions. And since they are much larger (typically >500 kDa) than a biomolecule, they may alter the function and trafficking of the target molecule, for example, steric hindrance introduced by such large tag may prevent the binding of the target molecule with its receptor. Also because of its large size, one QD carries multiple target molecules creating an artificial cluster which may lead to unphysiological consequences. Their proneness to aggregation and usually needed polymeric functional coating further exaggerates the aforementioned "size" issues.

Recently, graphene quantum dots (GQDs), which are individual single-atom-thick or a-few-atom-thick nanometer-sized planar sheet of graphitic carbon, have sparked significant excitement as a promising new class of fluorophores for bioimaging, owing to their interesting and tunable photoluminescence properties originated from quantum confinement, excellent photo-stability, biocompatibility, good water solubility, chemical inertness, small size, and low cost. Several groups have demonstrated that GQDs can be uptaken into live cells and remain fluorescent in various cellular locations without introducing apparent cytotoxicity, indicating the bioimaging capability of GQDs. In a pioneer work, Dai and coworkers have showed that the PEG-modified nanographene oxide sheets (~20 nm) functionalized with anti-CD20 can act as near-infrared fluorophores for selective recognition and imaging of CD20-expressing Raji B-cells (Liu Z, Robinson J T, Sun X M, Dai H J. *PEGylated nanographene oxide for delivery of water-insoluble cancer drugs. J Am Chem Soc* 2008, 130(33): 10876-10877).

Despite its highly anticipated potentials, GQDs have yet to be used to specifically label and track molecular targets involving in dynamic cellular processes in live cells.

BRIEF SUMMARY

It is herein demonstrated that graphene quantum dots (GQDs) can serve as a universal fluorophore for bioimaging because the GQDs can be readily conjugated with a wide range of biomolecules without interfering their activities. In a disclosed example, the use of insulin conjugated GQDs for real-time tracking of the dynamics of insulin receptors in 3T3-L1 adipocytes using total internal reflection microscopy (TIRFM) has been demonstrated. The experiments reveal that the internalization and recycling of insulin receptors in adipocytes were enhanced by apelin but inhibited by TNFα, providing evidence for the molecular mechanisms underlying the regulation of these cytokines on insulin sensitivity.

According to a first aspect of the invention, there is provided a method for coupling a biomolecule to a graphene quantum dot (GQD).

The method comprises contacting a solution containing GQD with 1-ethyl-3-(3-dimethylaminopropyl)carbodiimide hydrochloride (EDC) to obtain an O-acylisourea intermediate.

The method further comprises contacting the O-acylisourea intermediate compound with N-hydroxysuccinimide (NHS) to obtain a NHS ester.

The method further comprises contacting the NHS ester with a biomolecule for conjugation, thereby obtaining a biomolecule-GQD conjugate.

According to a second aspect of the invention, a fluorophore is described herein. The fluorophore comprises a biomolecule-GQD conjugate obtained by a method as described in the first aspect.

According to a third aspect of the invention, an imaging method is provided herein. The imaging method comprises administering a fluorophore of the second aspect to a subject.

The imaging method further comprises collecting imaging data of the subject or part of the subject with optical multimodality imaging.

BRIEF DESCRIPTION OF THE SEVERAL VIEWS OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DETAILED DESCRIPTION

Figure 1:
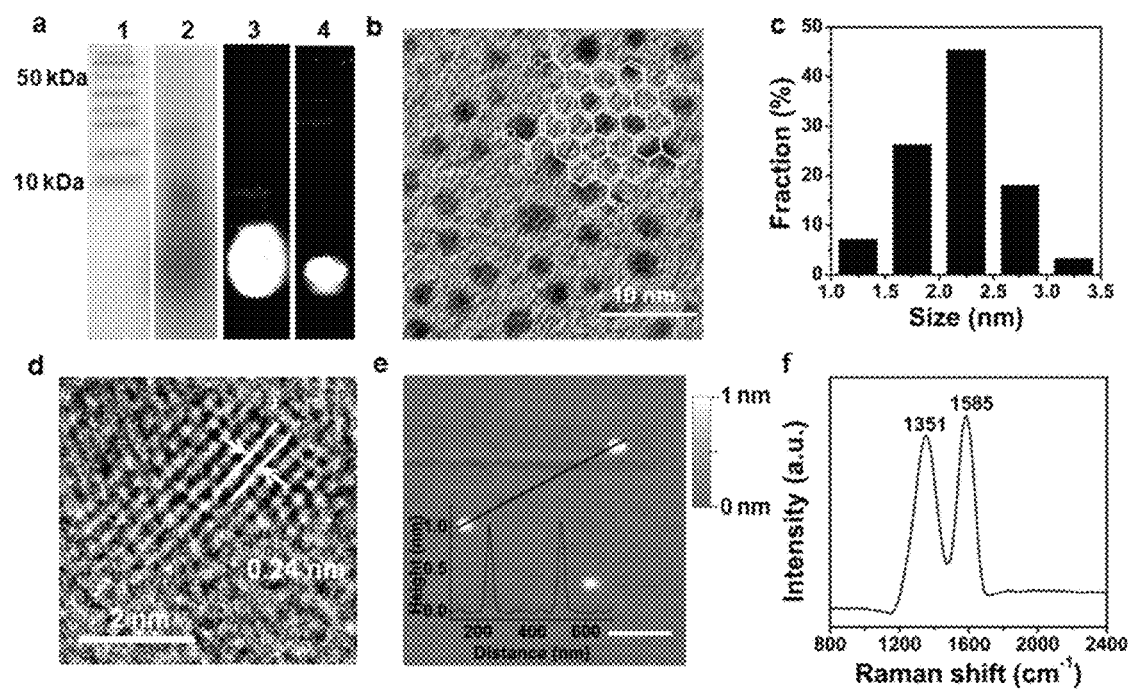
FIG. 1 shows GQD characterizations: (a) Electrophoretic separation of molecular weight markers (1), GQD (2&3), GQD after ultra-filtration (4). Lane 1 & 2 were imaged under white light while 3 & 4 was illuminated by a xenon lamp with a 488/505 nm filter; (b) TEM image of GQD. Inset shows the chemical structure of a GQD; (c) Size distribution of 180 GQDs; (d) High-resolution TEM image; (e) AFM image of GQDs. Inset shows the height profile along the red line. Scale bar=0.2 μm; (f), Raman spectrum of GQDs.

The following detailed description refers to the accompanying drawings that show, by way of illustration, specific details and embodiments in which the invention may be practised. These embodiments are described in sufficient detail to enable those skilled in the art to practise the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

Owing to their interesting and tunable photoluminescence properties originated from quantum confinement, excellent photo-stability, biocompatibility, good water solubility, chemical inertness, small size, and low cost, graphene quantum dots (GQDs) are herein described for specifically labelling and tracking molecular targets involved in dynamic cellular processes in live cells. In particular, the GQDs are conjugated to biomolecules.

While present invention describes a method to conjugate biomolecule to GQDs, other chemistry methods used for functionalizing carbon materials (e.g., graphene, carbon nanotubes, graphite, etc) may also be applicable.

GQDs can be synthesized through various top-down or bottom-up routes. The former involves cleaving or breaking down of large carbonaceous materials via physical, chemical or electrochemical techniques. The latter is realized by pyrolysis or carbonization of small organic molecules or by step-wise chemical fusion of small aromatic molecules. The synthesized GQDs can be further chemically modified or doped with heteroatoms to attain new or improved properties.

Thus, in accordance with a first aspect, a method for coupling a biomolecule to a graphene quantum dot (GQD) is described.

In this context, the term "biomolecule" refers to biological material including tissue fragments comprising a mass of cells, multi-cell organisms and structures, a single cell and subcellular structures. The term is also used interchangeably with other equivalent terms, such as "bio-molecular body". Examples of eukayotic cells include both plant and animal cells. Examples of some animal cells include cells in the nervous system such as astrocytes, oligodendrocytes, Schwann cells; autonomic neuron cells such as cholinergic neural cell, adrenergic neural cell, and peptidergic neural cell; sensory transducer cells such as olfactory cells, auditory cells, photoreceptors; hormone secreting cells such as somatotropes, lactotropes, thyrotropes, gonadotropes and corticotropes from the anterior pituitary glands, thyroid gland cells and adrenal gland cells; endocrine secretory epithelial cells such as mammary gland cells, lacrimal gland cells, ceruminous gland cells, eccrine sweat glands cells, and sebaceous gland cells; and other cells including osteoblasts, fibroblasts, blastomeres, hepatocytes, neuronal cells, oocytes, blood cells such as erythrocytes, lymphocytes or monocytes, muscle cells such as myocytes, embryonic stem cells. Other examples of eukaryotic cells include yeast cells and protozoa. Examples of plant cells include meristematic cells, parenchyma cells, collenchyma cells and sclerenchyma cells. Prokaryotic cells include, for example, archaea cells and bacteria cells. The term biomolecule additionally encompasses other types of biological material such as subcellular (intracellular) structures such as the nucleus, nucleolus, endoplasmic reticulum, centrosome, cytoskeleton, Golgi apparatus, mitochondrion, lysosome, peroxisome, vacuole, cell membrane, cytosol, cell wall, chloroplast, and fragments, derivatives, and mixtures thereof.

First, a solution containing GQD is prepared. The solution may be prepared by any known method. For example, the GQDs may be synthesized as described in Dong Y Q, et al. *J Mater Chem* 2012, 22(18): 8764-8766.

Next, the solution containing the GQD is contacted with 1-ethyl-3-(3-dimethylaminopropyl)carbodiimide hydrochloride (EDC). The GQD solution may be added to the EDC. Alternatively, the EDC may be added to the GQD solution. Yet alternatively, the GQD solution and EDC may be individually added to a common container. In other words, the order of mixing or adding the two components does not matter.

GQD contains carboxyl groups on the edge. By reacting EDC with the GQD, an amine reactive O-acylisourea intermediate compound is obtained.

The O-acylisourea intermediate compound is unstable due to its susceptibility to hydrolysis.

Thus, in a next step of the method, the O-acylisourea intermediate compound is contacted with N-hydroxysuccinimide (NHS). The O-acylisourea intermediate compound may be added to the NHS. Alternatively, the NHS may be added to the O-acylisourea intermediate compound. Yet alternatively, the O-acylisourea intermediate compound and NHS may be individually added to a common container. In other words, the order of mixing or adding the two components does not matter.

The NHS converts the unstable O-acylisourea intermediate compound to an amine reactive NHS ester.

Thereafter, in a further step the NHS ester modified GQD is contacted with a biomolecule for conjugation, thereby obtaining a biomolecule-GQD conjugate. The NHS ester modified GQD may be added to a solution containing the biomolecule. Alternatively, the biomolecule may be added to the NHS ester modified GQD. Yet alternatively, the NHS ester modified GQD and the biomolecule may be individually added to a common container. In other words, the order of mixing or adding the two components does not matter.

The conjugation occurs due to the NHS ester modified GQD covalently reacted with the amine groups of the biomolecule such as proteins or peptides.

In a further step to convert the excess NHS ester into hydroxamic acid, the biomolecule-GQD conjugate is contacted with hydroxylamine solution to quench the reaction. The biomolecule-GQD conjugate may be added to the hydroxylamine solution. Alternatively, the hydroxylamine solution may be added to the biomolecule-GQD conjugate. Yet alternatively, the biomolecule-GQD conjugate and the hydroxylamine solution may be individually added to a common container. In other words, the order of mixing or adding the two components does not matter.

Figure 2:
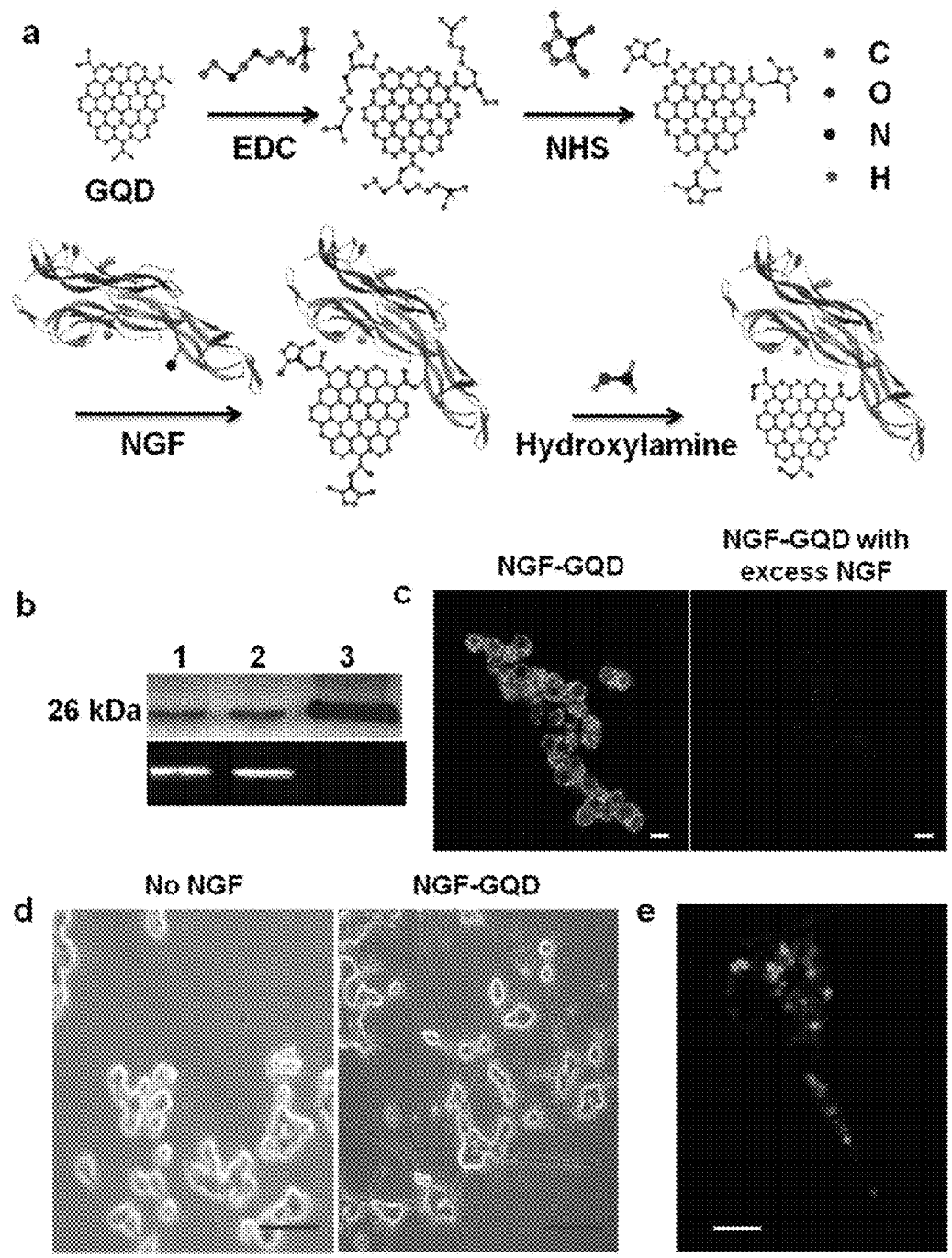
FIG. 2 shows NGF-GQD is biologically functional: (a) Schematic illustration of conjugating GQD with NGF; (b) Gel electrophoresis of NGF-GQD (lane 1), FITC-NGF (lane 2) and NGF (lane 3); (c) Fluorescence images of living PC12 cells incubated with 200 ng/mL NGF-GQD (left) or NGF-GQD together with 20 µg/mL free NGF (right) for 15 min; (d) Representative phase-contrast images of PC12 cells after 2-day incubation without (left) or with 200 ng/mL of NGF-GQD (right). Scale bar=50 µm; (e) Distribution of NGF-GQD in PC12 cells differentiated by 200 ng/mL NGF-GQD for 24 h. Scale bar=5 µm.

An outline of the conjugation method is illustrated in FIG. 2, whereby in one example the biomolecule conjugated to the GQD is a nerve growth factor (NGF).

One advantage of forming the biomolecule-GQD conjugate by the method described herein is that the GQD is conjugated to the biomolecule without a cross-linker in between the two entities which may otherwise intervene with the functionalities of either entity.

As mentioned above, in one embodiment the biomolecule comprises nerve growth factor (NGF).

In various other embodiments, the biomolecule comprises insulin, neuropeptide Y, bovine serum albumin, immunoglobulin G, or concanavalin A.

In another embodiment, the biomolecule is insulin.

A second aspect relates to a fluorophore.

The fluorophore comprises a biomolecule-GQD conjugate obtained by a method as described above.

In one embodiment, the fluorophore comprises an insulin-GQD conjugate.

In another embodiment, the fluorophore comprises a NFG-GQD conjugate.

This invention further describes an application of GQDs for conventional single-photon fluorescent imaging. Some GQDs have excellent up-conversion property (emitting shorter wavelength upon simultaneous absorption of two or sequential absorption of multiple longer wavelength photons), which is desirable for in vivo imaging because of deep-tissue penetration ability of long excitation wavelength (e.g. NIR), and for molecular imaging with high spatial-resolution, low back ground interference, and low photon-induced toxicity because of the highly-localized nonlinear photon adsorption process.

In other words, the fluorophore may be used in an imaging method.

Therefore, in a third aspect, an imaging method is described. The imaging method comprises administering a fluorophore to a subject, wherein the fluorophore is as described above.

The imaging method further comprises collecting imaging data of the subject or part of the subject with optical imaging.

Sometimes, it may be beneficial to provide an imaging method involving an optical multimodality imaging.

Generally, a multimodal imaging system is a medical imaging system that combines optical, radioactive and magnetic imaging modes. This method of imaging may include modes such as positron emission topography, optical fluorescence and bioluminescence as well as magnetic resonance spectroscopy and single photon emission topography. For example, multimodal imaging combines elements of MRI and PET scans as well as imaging tests with radioactive elements that illuminate imagery inside a body of the subject. Different methods may be used to study the subject or part of a subject, for example human tissue, at the same time; thereby allowing medical doctors to see multiple aspects of the same area, for example, to see anything present in that specific tissue: its size, its exact location and its metabolic activity. This would then allow for analysis of the metabolic activity of surrounding tissues and evaluation of abnormalities or changes in the function of those tissues as a result of a condition or any other medical complication.

In various embodiments, the imaging method is ex vivo imaging.

In various embodiments, the imaging method includes confocal fluorescence imaging.

In various embodiments, the imaging method is carried out on a mammalian subject.

In one embodiment, the part of the subject where the imaging method is carried out is a mammalian adipocyte cell.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

In order that the invention may be readily understood and put into practical effect, particular embodiments will now be described by way of the following non-limiting examples.

EXAMPLES

Experimental Section
GQD Synthesis and Characterization

The precursor, carbon black (0.2 g, Vulcan CX-72, Cabot Corporation), was refluxed with nitric acid (50 mL, 6 M) for 24 h. After centrifugation (2770 g, 10 min), the supernatant was heated to yield a reddish brown powders, which was then re-suspended in DI water and filtered through a 0.22 μm microporous membrane. The colloidal solution was further ultra-filtered through a centrifugal filter device using a filtering membrane with cut-off molecular weight of 3 kDa (Amicon Ultra-4, Millipore) for 40 min. The strongly fluorescent GQDs were obtained in the filtrate. Transmission electron microscopy (TEM) was conducted on a JEOL (JEM 2010) electron microscope at an acceleration voltage of 200 kV. GQDs were also characterized with tapping-mode atomic force microscopy (AFM) (MFP-3D, Asylum Research) using a NCH20 tip (silicon cantilever, Nanoworld). Raman spectra were recorded at ambient temperature on a WITeck CRM200 confocal microscopy Raman system with 633 nm laser.

GQD Bio-conjugation

GQD solution (0.5 mg/mL) was first mixed with 1-ethyl-3-(3-dimethylaminopropyl)carbodiimide hydrochloride (EDC, 10 mM) and N-hydroxysuccinimide (NHS, 10 mM) for 15 min. NGF or insulin (0.1 mg/mL) was subsequently added into the above mixture for 4 h at room temperature. The reaction was quenched by adding hydroxylamine (10 mM). The obtained samples were ultra-filtered three times (centrifuging at 7500 g for 20 min) with PBS to remove free unconjugated GQDs. The conjugated GQD samples were then separated in the 10-12% SDS polyacrylamide gels at 140 V for 40 min and imaged with a gel imaging system (ProXPRESS 2D, Pekin Elmer) to confirm the successful bio-conjugation.

Fourier transform infrared spectroscopy (FTIR) was performed with a Perkin Elmer FT-IR Spectrum GX. Spectroscopic properties of GQD samples were characterized by UV-vis spectrophotometer (Nanodrop 2200c, Thermo Scientific) and fluorospectrometer (Nanodrop 3300). The zeta potential of GQD samples was measured using a Zetasizer 3000 (Malvern Instruments).

Confocal Fluorescence Imaging

PC12 cells were incubated with NGF-GQD (200 ng/mL) for 15 min or 24 h, then washed. For the competitive assay, excess free NGF (20 μg/mL) were added to the PC12 cells for 10 min, followed by the addition of NGF-GQD. 3T3-L1 adipocytes were untreated, or pre-treated with TNFα (50 ng/mL) or pyr-apelin-13 (1 μM) for 1 h at 37° C., followed by incubation with insulin-GQD (10 μg/mL) for 10 min or 1 h. Adipocytes were washed, fixed with 4% formaldehyde in ice-cold PBS, and imaged using a confocal microscope (Zeiss LSM 510) with a 63× oil objective and a 488 nm laser. For immuno-staining experiment, after 3T3-L1 adipocytes being fixed, insulin receptors were stained in PBS-Tween solution with specific rabbit anti-insulin receptor IgG (C-terminal of β-subunit, Santa Cruz Biotech) overnight followed by incubation with anti-rabbit IgG conjugated with Atto647 NHS (Sigma) and 10 μg/mL insulin-GQD for 1 h.

Total Internal Reflection Fluorescence Microscopy (TIRFM)

The adipocytes were incubated with insulin-GQD for 10 min or 1 h at 37° C. prior to imaging. The cells were washed and incubated in a bath solution (150 mM NaCl, 5 mM KCl, 1.1 mM $MgCl_2$, 2.6 mM $CaCl_2$, 10 mM HEPES, and 10 mM glucose, pH 7.4) during imaging. Time-lapse images (241 frames, 0.5 s/frame) were recorded at 37° C. using an inverted TIRFM microscope (Axiovert 200, Carl Zeiss) with a 100× oil objective (NA=1.45) and a charge coupled device camera (CCD, pixel size=0.248 μm).

Quantum Yield (QY) Measurement

Fluorescein in water (QY=0.79) was chosen as the standard. The quantum yield of GQDs (in water) was calculated according to: $\phi_x = \phi_{st}(I_x/I_{st})(\eta_x^2/\eta_{st}^2)(A_{st}/A_x)$, where φ is the quantum yield, I is the measured integrated emission intensity, η is the refractive index of the solvent, and A is the optical density. The subscript "st" refers to the standard and "x" for the sample.

Cytotoxicity Test

Figure 7:
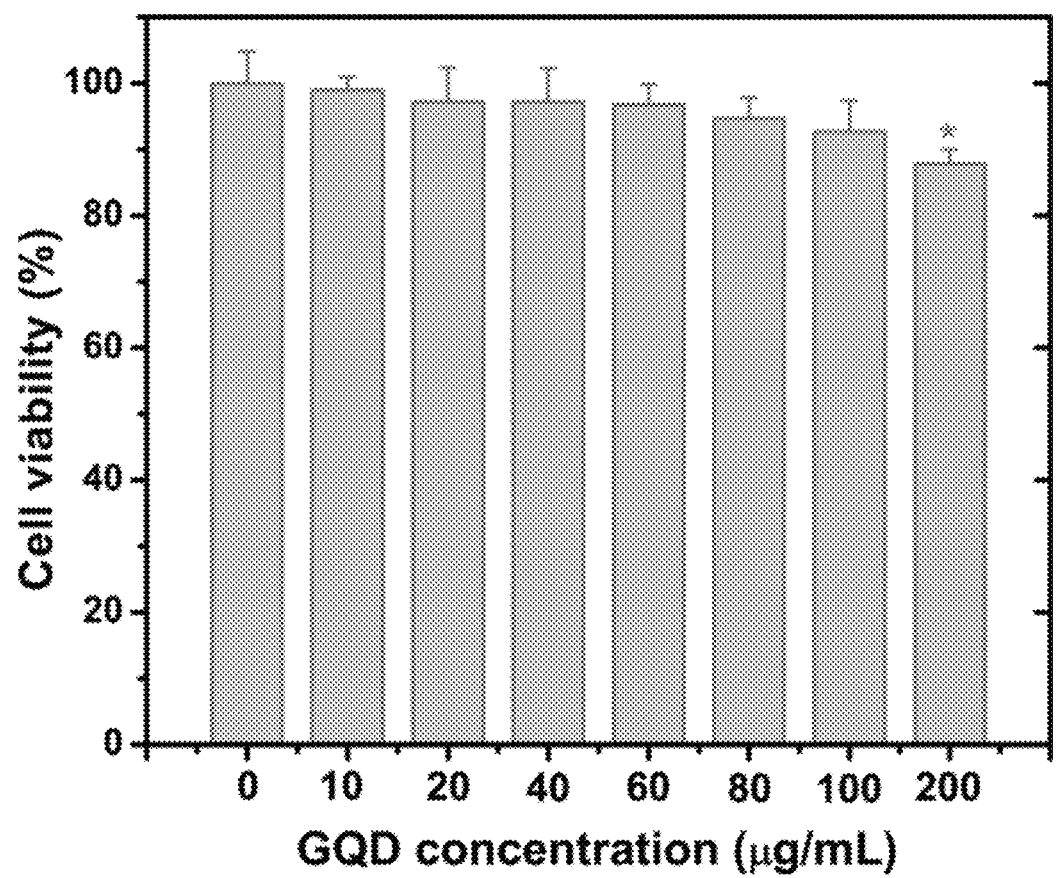
FIG. 7 shows the viability of cells and biocompatibility of the GQDs.

The viability of cells were evaluated using 3-[4,5-dimethylthialzol-2-yl]-2,5-diphenyltetrazolium bromide (MTT) assay (FIG. 7). Briefly, PC12 cells were seeded into 96-well plates at a density of 1×10⁴ per well in 200 μL of media for 24 h. The cells were then incubated with various concentrations of GQDs (0, 10, 20, 40, 60, 80, 100, 200, 400 μg/mL) for 24 h. Then, MTT solution (20 μL, 5 mg/mL) was added to each well for 4 h. Thereafter, the MTT solution was removed and the precipitated violet crystals were dissolved in 200 μL of DMSO. The absorbance at 570 nm was measured using a BioTek microplate reader.

Cell Culture

PC 12 cells were incubated in RPMI 1640 medium (Invitrogen) with 10% fetal bovine serum, 5% horse serum, and 1% penicillin-streptomycin (37° C., 5% $CO_2$). Mouse 3T3-L1 pre-adipocytes purchased from American Type Culture Collection (Rockville, Md., USA) were cultured in Dulbecco's modified Eagle's medium (DMEM, Gibco) containing 10% (v/v) heat-inactivated fetal bovine serum (FBS; Gibco) and 1% penicillin-streptomycin (37° C., 5% $CO_2$).

Adipocyte Differentiation

3T3-L1 pre-adipocytes were differentiated into adipocytes as described previously. After 3T3-L1 pre-adipocytes reaching confluence (defined as day 0), the cells were cultured in DMEM containing 10% FBS, 10 μg/mL insulin, 0.5 mM isobutyl-1-methyl xanthine and 1 μM dexamethasone for the first 2 days, and changed to DMEM with 10% FBS and 10 μg/mL insulin for another 2 days. Cells were then maintained in DMEM with 10% FBS for 4-5 days. Most of the cells were differentiated on day 8 as confirmed by appearance of intracellular lipid droplets.

Results

GQDs were synthesized as previously reported (Dong Y Q, et al. One-step and high yield simultaneous preparation of single- and multi-layer graphene quantum dots from CX-72 carbon black. J Mater Chem 2012, 22(18): 8764-8766). But as shown in FIG. 1(a), the as-prepared GQDs separate into a fast-moving fluorescent band and slow-moving non-fluorescent band by gel electrophoresis, indicating the existence of two heterogeneous populations differing in size. Therefore, ultra-filtration was used to eliminate larger non fluorescent species. As shown in FIG. 1(a), the purified GQDs exhibits a narrow fluorescent band after electrophoresis, indicating the improved uniformity in size distribution. And the comparison with the blots from the known protein markers suggest that the electrophoretic mobility (thus probably the size) of the purified GQDs is comparable to a protein of a few kDa. The quantum yield of the purified GQDs is measured to be ~14.3%, which is much higher than that of the as-prepared GQDs (~4.04%).

As revealed by transmission electron microscopy (TEM), the obtained GQDs have an average diameter of ~2.2 nm with a narrow size distribution (FIG. 1(b), 1(c)). The molecular weight of such a GQD (2.2 nm atomic carbon-sheet) is estimated to be ~2 kDa, consistent with the observation from gel electrophoresis. This molecular weight is desirably much smaller than a 6 nm CdSe quantum dot (~500 kDa) and the commonly used green fluorescent protein (27 kDa). It is also much smaller than most macromolecules in a cell. The high resolution TEM (HRTEM) image (FIG. 1(d)) shows that the GQDs exhibit high crystallinity with a lattice spacing of 0.24 nm corresponding to (1120) lattice fringes of graphene. AFM image reveals that the topographic height of a GQD is ~1 nm, in agreement with the thickness of single-layer graphene (FIG. 1(e)). FIG. 1(f) presents the Raman spectrum of the GQDs which exhibits two characteristic peaks at 1351 and 1585 cm$^{-1}$, corresponding to the D and G band of graphene, respectively. The $I_D/I_G$ ratio (ca. 0.9) is similar to that of graphene oxides (GO) (Gao W, Alemany L B, Ci L J, Ajayan P M. *New insights into the structure and reduction of graphite oxide. Nat Chem* 2009, 1(5): 403-408), suggesting that, similar to GO, there are oxygenated groups on GQD which may serve as the convenient chemical handles for functionalization. Confirming the previous reports, it is also shown herein that GQD is highly biocompatible, specifically, a dose as high as (100 μg/mL) does not introduce obvious cytotoxicity (FIG. 7).

FIG. 2(a) illustrates a general route for functionalization of a protein or peptide with a GQD using nerve growth factor (NGF) as an example. First, 1-ethyl-3-(3-dimethylaminopropyl)carbodiimide hydrochloride (EDC) is applied to react with the carboxyl groups on the edge of GQD, forming an amine-reactive O-acylisourea intermediate. This intermediate is unstable due to its susceptibility to hydrolysis. Therefore, N-hydroxysuccinimide (NHS) is subsequently added to convert it to an amine-reactive NHS ester. The NHS ester modified GQD can then covalently react with the amine groups universally available in most proteins and peptides. Lastly, hydroxylamine is added to convert the remaining NHS esters into hydroxamic acids, thereby quenching the reaction. In this way, GQD is conjugated with a molecule without cross-linker in between which may otherwise intervene the functionalities of the molecule. Such zero-length cross-linker strategy has been previously used to conjugate PEG-amine to the carboxylic groups on graphene oxide. Using this facile bioconjugation method, it is verified that all the tested proteins can be successfully coupled with GQD, including neuropeptide Y, bovine serum albumin, immunoglobulin G, concanavalin A, insulin, and NGF.

To further demonstrate that GQD can serve as a universal fluoro-tag, the NGF conjugated GQD (NGF-GQD) was evaluated. As shown in FIG. 2(b), the electrophoretic mobility of NGF-GQD is similar to that of FITC (~0.4 kDa) labeled NGF and native NGF (~26 kDa), indicating that the attachment of GQD does not significantly increase the overall weight of the conjugate and GQD does not pair with multiple NGF molecules. In contrast to the large semiconductor QDs which cannot realize one-to-one conjugation, GQD is comparable to small fluorophores such as FITC, yet much more stable.

To show that the conjugated NGF retains its functionality, the ability of NGF-GQDs to bind specifically with NGF receptors abundantly expressed in neuroendocrine PC12 cells is examined. As demonstrated by the confocal fluorescence image shown in FIG. 2(c), PC12 cells incubated with 200 ng/mL NGF-GQD for 15 min show numerous bright fluorescent puncta both on cell membrane and in cytosol, presumably resulting from the binding of NGF-GQD with NGF receptors on the cell membrane and rapid internalization of the activated receptor complex (Cui B X, et al. *One at a time, live tracking of NGF axonal transport using quantum dots. Proc Natl Acad Sci USA* 2007, 104(34): 13666-13671; Rajan S S, Liu H Y, Vu T Q. *Ligand-bound quantum dot probes for studying the molecular scale dynamics of receptor endocytic trafficking in live cells. ACS nano* 2008, 2(6): 1153-1166). In the control experiment, when overwhelming free NGF molecules were added together, NGF-GQD staining was completely eliminated due to competitive inhibition (FIG. 2(c)). This unambiguously demonstrates the specific recognition between NGF-GQD and the NGF receptors. Furthermore, FIG. 2(d) shows that NGF-GQD was able to stimulate neurite outgrowth in PC12 cells, verifying that the NGF-GQD conjugate is capable of activating NGF signaling pathway. In the neuronal differentiated PC12 cells by NGF-GQD, the fluorescent NGF-GQD was observed to distribute in the cell body and along the neurites (FIG. 2(e)), similar to the previous report using NGF functionalized CdSe/ZnS QD (Vu T Q, et al. *Peptide-conjugated quantum dots activate neuronal receptors and initiate downstream signaling of neurite growth. Nano Lett* 2005, 5(4): 603-607).

Thus far, it has been demonstrated the potential of GQD as a universal small fluorophore that can be conveniently and covalently tagged with any amine-bearing biomolecule without impairing its functionalities. As a more careful case study and a proof-of-concept demonstration of using GQD for biological studies, it is further sought to demonstrate the use of insulin-GQD to label and track the dynamics of insulin receptors in adipocytes (fat cells) in physiological context for the first time.

Figure 3:
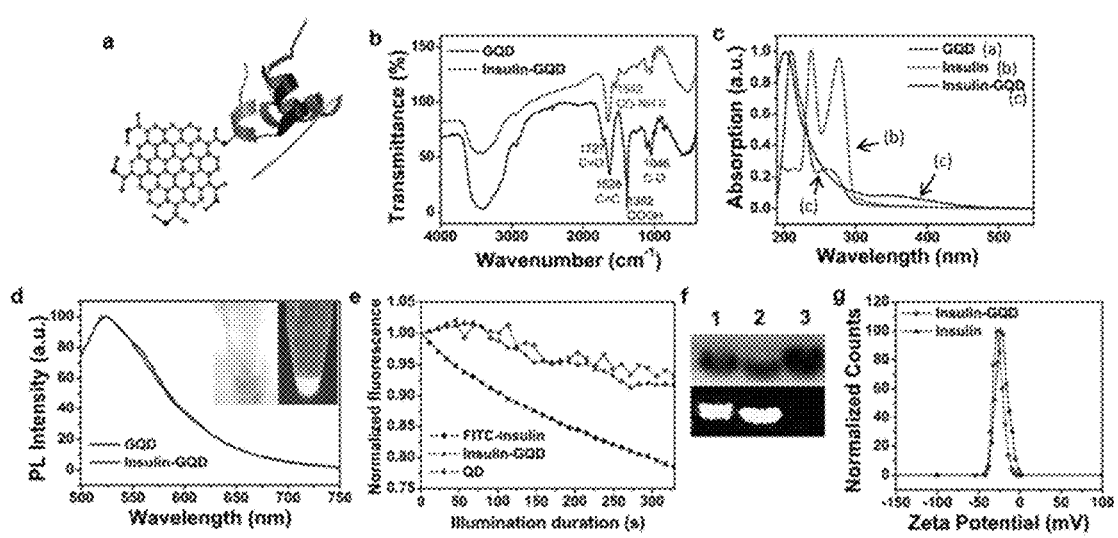
FIG. 3 shows characterization of insulin-GQD conjugates: (a) Illustration of insulin-GQD; (b) FTIR spectra of GQD and insulin-GQD; (c) UV-vis absorption spectra of GQD, insulin and insulin-GQD; (d) Photoluminescence (PL) spectra of GQD and insulin-GQD. The excitation wavelength is 488 nm. Inset shows the optical and fluorescent images of Insulin-GQD aqueous suspension; (e) Photobleaching profile of insulin-FITC, insulin-GQD and CdTe-QD; (f) Gel electrophoresis of insulin-GQD (lane 1), insulin-FITC (lane 2) and insulin (lane 3); (g) Zeta potential of insulin and Insulin-GQD at pH 7.

The Fourier transform infrared (FTIR) spectrum (FIG. 3(b)) reveals the existence of C=O (1727 cm$^{-1}$), C=C (1628 cm$^{-1}$), COOH (1382 cm$^{-1}$) and C—O (1046 cm$^{-1}$) functional groups in GQD. In the insulin-GQD conjugates, the COOH peak diminishes while a new peak appears at 1542 cm$^{-1}$ corresponding to the formation of an amide linkage, confirming that the COOH groups are used to form conjugation with insulin. As shown in the UV-vis spectra (FIG. 3(c)), GQD has an absorption peak at 202 nm while insulin exhibits the absorption peaks at 237 and 276 nm. In comparison, insulin-GQD has an absorption maximum at 209 nm with two shoulders at 224 nm and 267 nm, further verifying the successful conjugation of insulin with GQD.

Both bare GQD and insulin-GQD in PBS solution are light-yellow under daylight and give olivine fluorescence upon excitation at 488 nm (FIG. 3(d)). The photoluminescence spectra of GQD and insulin-GQD are similar with an emission peak at ~520 nm (FIG. 3(d)), suggesting that the photoluminescence property of GQD has little change after the conjugation. And as shown in FIG. 3(e), the fluorescence of insulin-GQDs only gradually declines over time due to photo-bleaching (1.4%/min) whereas a precipitous decay in fluorescence is observed for FITC labeled insulin (insulin- FITC). The photo-bleaching rate of GQD is similar to that of CdTe QD. Thus, GQD can be considered as a photo-stable label suitable for long-term fluorescence tracking experiments. As shown in FIG. 3(f), insulin-GQD conjugates shows similar gel mobility to that of insulin-FITC and insulin itself (~5.8 kDa), implying one-to-one pairing between insulin and GQD and that GQD tag does not significantly affect the charge state of insulin. The latter is also confirmed by the observation that the zeta potential of insulin-GQD (−26.0±6.07 mV, n=3) is similar to that of insulin (−21.1±7.3 mV, n=3) (FIG. 3(g)). The desired one-to-one pairing between GQD and insulin can be attributed to the electrostatic repulsion between negatively charged insulin molecules and the fact that the size of a GQD is comparable to the Debye charge screening length in physiological condition.

Insulin signaling, mediated by insulin receptors (IRs), plays a central role in the regulation of cellular glucose metabolism as well as other functions. Impaired response to insulin is the hallmark of diabetes while excessive insulin activity is correlated with cancers. Binding between insulin and IR at the plasma membrane triggers receptor internalization and recycling. The inefficiency of such receptor turnover is associated with insulin resistance which is a notorious cause to many diseases (e.g., type 2 diabetes). Although revealing the trafficking dynamics of IR is of obvious importance, it remains challenging and poorly-studied partly due to the lack of labeling method for live cell imaging.

Previous studies have provided evidence that TNFα (a pro-inflammatory factor) induces insulin resistance and apelin (a novel signaling peptide expressed in various cell types including adipocytes) is able to improve insulin sensitivity. However, the underlying mechanisms of how these cytokines act, particularly their influences on insulin receptors, are still elusive.

Figure 4:
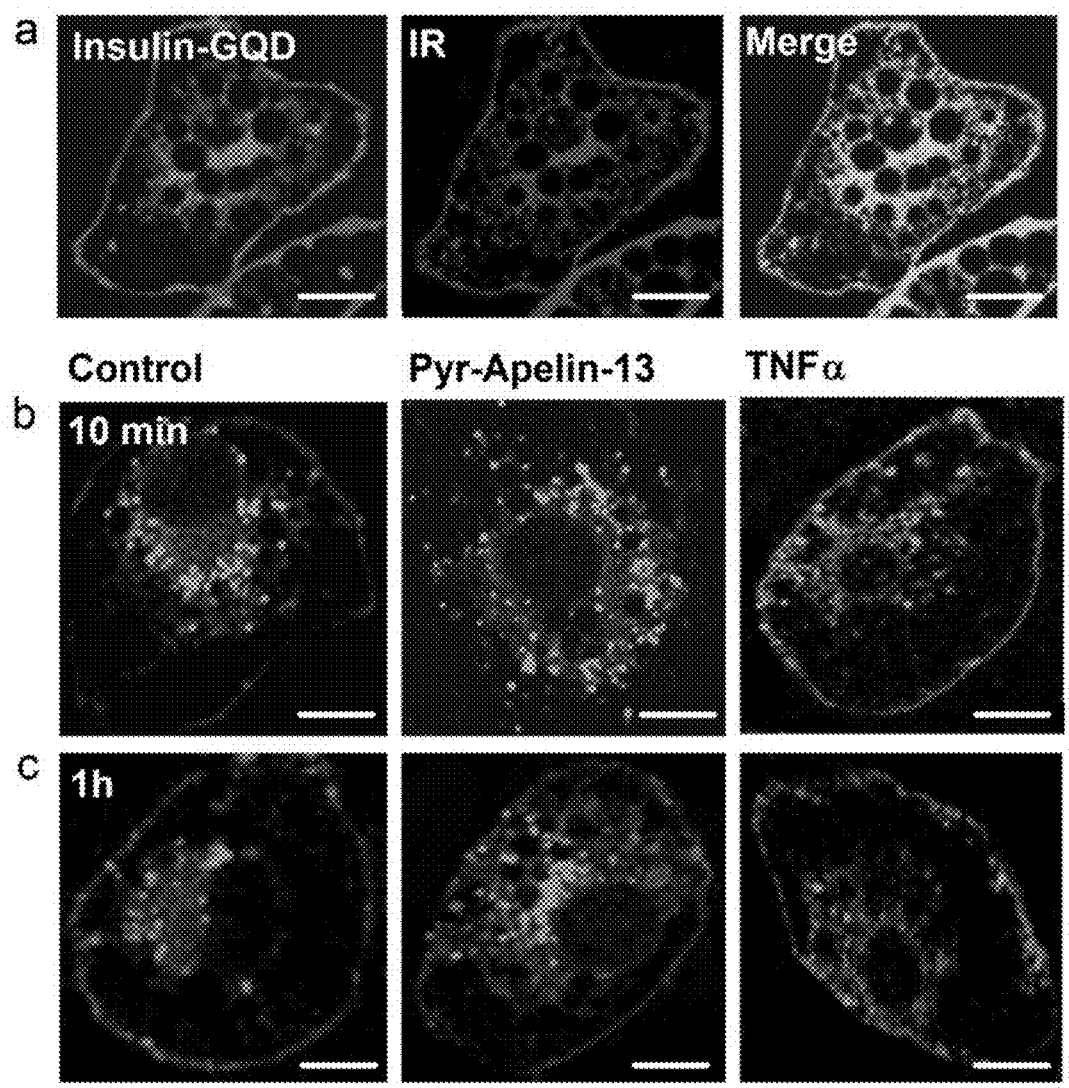
FIG. 4 shows confocal fluorescence imaging of insulin receptor in 3T3-L1 adipocytes: (a) Representative confocal fluorescence images of a fixed and permeabilized adipocyte labeled with insulin-GQDs (green, left), or with antibodies against insulin receptor β subunit followed by Atto647 NHS conjugated secondary antibodies (red, middle). The merged image is shown on the right. Scale bar=10 µm; (b), (c) Confocal fluorescence images showing the cellular distribution of insulin receptors in control, pyr-apelin-13 (1 µM) or TNFα (50 ng/mL) treated adipocytes after (b) 10 min or (c) 1 h incubation with insulin-GQDs.
Figure 5:
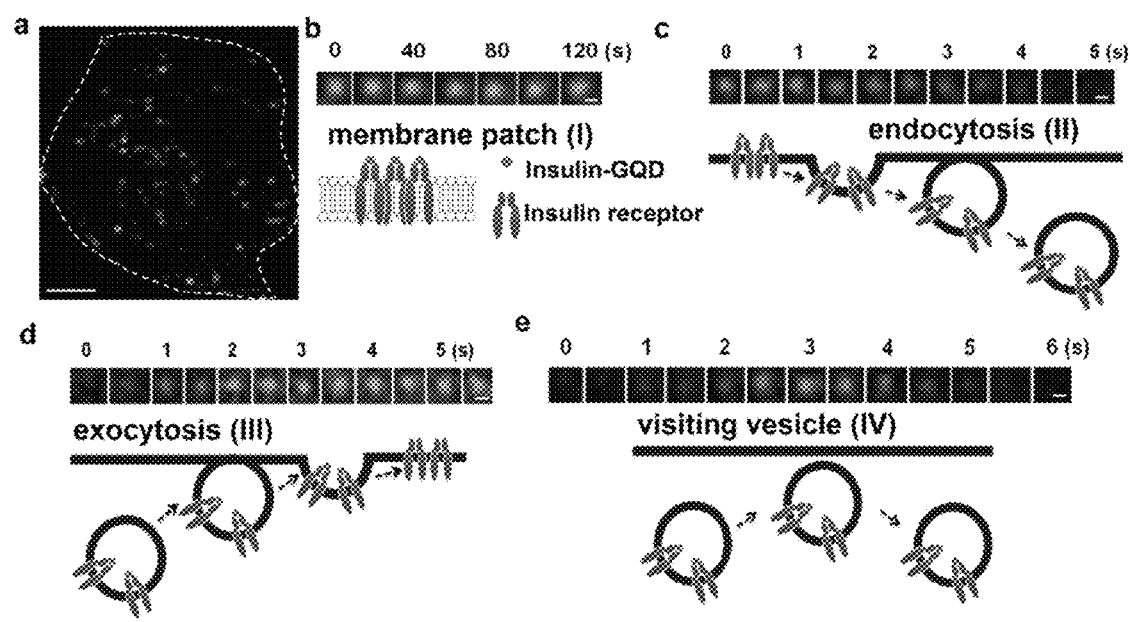
FIG. 5($a$)-($e$) shows cell imaging according to one embodiment of this disclosure.
Figure 6:
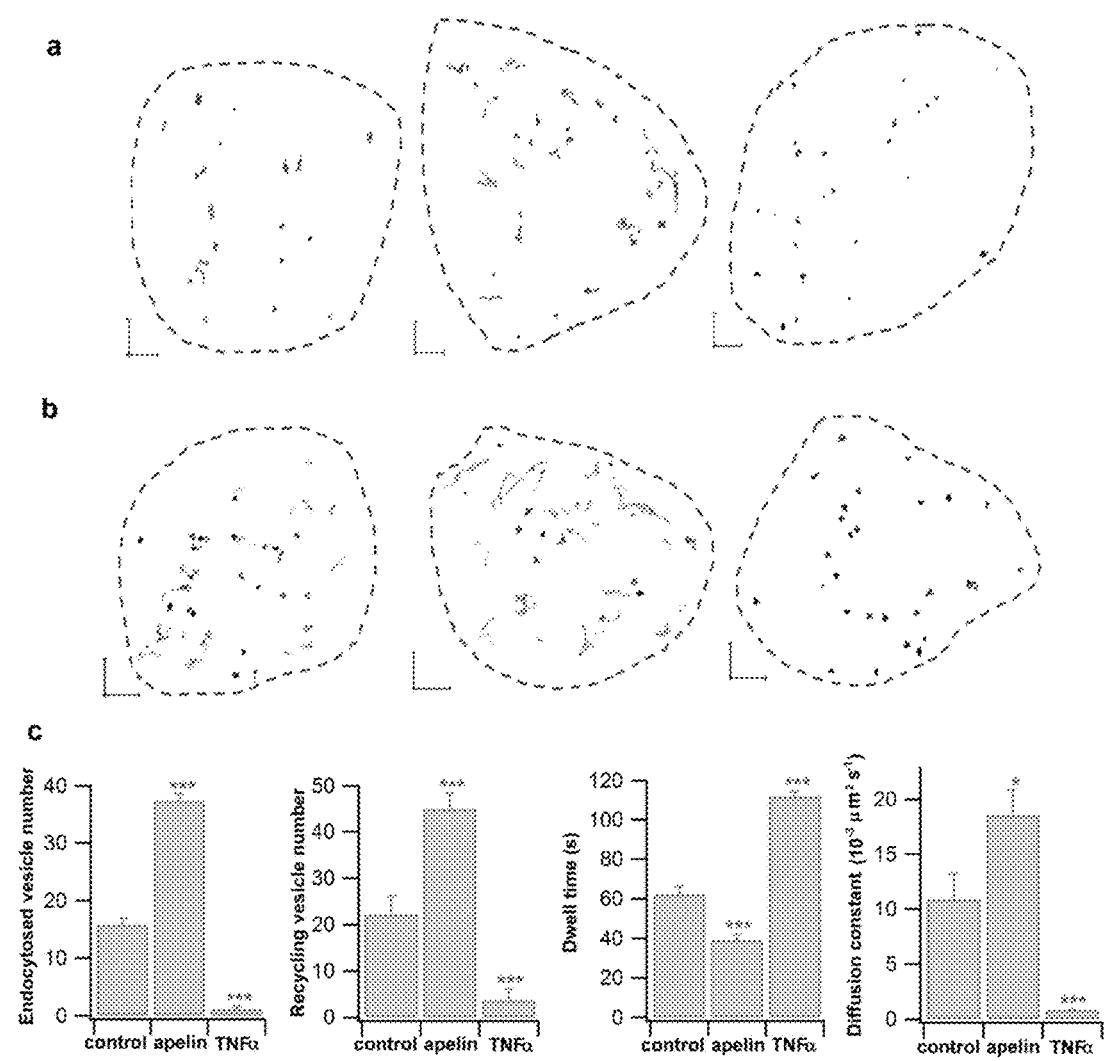
FIG. 6($a$)-($c$) shows cell imaging according to another embodiment of this disclosure.

As observed by confocal fluorescence imaging (FIG. 4(a)), incubation (1 h) of insulin-GQD with fixed and permeablized 3T3-L1 adipocytes results in cellular staining perfectly co-localized with immunostaining using IR-specific primary antibodies and fluorophore (Atto647 NHS) conjugated secondary antibodies, indicating the ability of insulin-GQD to specifically label IR and reveal its cellular distribution. As shown, IRs abundantly reside in the cell membrane and also scatter in the cytosol.

Confocal analyses of IR localization were then performed with short-time incubation (10 min) of insulin-GQD with live adipocytes (control, or pre-treated with apelin or TNFα) followed by cell fixation. In control cells, most IRs are found in the cell interior while a small fraction of them remain on the plasma membrane, indicating that the majority of IRs receptors are quickly (within 10 min) internalized (or endocytosed) into cytoplasm upon binding with insulin-GQD (FIG. 4(b)). In comparison, insulin stimulated IR internalization is largely enhanced by apelin treatment whereas inhibited by TNFα (FIG. 4(b)). Evidently, apelin and TNFα regulates IR trafficking oppositely, in consistent with their effects on insulin sensitivity. As the insulin-GQD incubation time is extended to 1 h, membrane staining with GQD re-appears for control and apelin-treated cells, suggesting the recycling of IRs back to the plasma membrane (FIG. 4(c)).

REFERENCES

1. Michalet X, et al. Quantum dots for live cells, in vivo imaging, and diagnostics. Science 2005, 307(5709): 538-544.

2. Zhang J, Campbell R E, Ting A Y, Tsien R Y. Creating new fluorescent probes for cell biology. Nat Rev Mol Cell Biol 2002, 3(12): 906-918.

3. Lukinavičius G, et al. A near-infrared fluorophore for live-cell super-resolution microscopy of cellular proteins. Nat Chem 2013, 5(2): 132-139.

4. Resch-Genger U, Grabolle M, Cavaliere-Jaricot S, Nitschke R, Nann T. Quantum dots versus organic dyes as fluorescent labels. Nat Methods 2008, 5(9): 763-775.

5. Vu T Q, et al. Peptide-conjugated quantum dots activate neuronal receptors and initiate downstream signaling of neurite growth. Nano Lett 2005, 5(4): 603-607.

6. Jiang S, Liu A P, Duan H W, Soo J, Chen P. Labeling and Tracking P2 Purinergic Receptors in Living Cells Using ATP-Conjugated Quantum Dots. Adv Funct Mater 2011, 21(14): 2776-2780.

7. Pinaud F, Clarke S, Sittner A, Dahan M. Probing cellular events, one quantum dot at a time. Nat Methods 2010, 7(4): 275-285.

8. Pan D Y, Zhang J C, Li Z, Wu M H. Hydrothermal Route for Cutting Graphene Sheets into Blue-Luminescent Graphene Quantum Dots. Adv Mater 2010, 22(6): 734-738.

9. Jin S H, Kim D H, Jun G H, Hong S H, Jeon S. Tuning the Photoluminescence of Graphene Quantum Dots through the Charge Transfer Effect of Functional Groups. ACS nano 2012.

10. Tetsuka H, et al. Optically Tunable Amino-Functionalized Graphene Quantum Dots. Adv Mater 2012, 24(39): 5333-5338.

11. Zhuo S J, Shao M W, Lee S T. Upconversion and Downconversion Fluorescent Graphene Quantum Dots: Ultrasonic Preparation and Photocatalysis. ACS nano 2012, 6(2): 1059-1064.

12. Shen J, Zhu Y, Yang X, Li C. Graphene quantum dots: emergent nanolights for bioimaging, sensors, catalysis and photovoltaic devices. Chem Commun 2012, 48(31): 3686-3699.

13. Dong Y Q, et al. Blue luminescent graphene quantum dots and graphene oxide prepared by tuning the carbonization degree of citric acid. Carbon 2012, 50(12): 4738-4743.

14. Lin L X, Zhang S W. Creating high yield water soluble luminescent graphene quantum dots via exfoliating and disintegrating carbon nanotubes and graphite flakes. Chem Commun 2012, 48(82): 10177-10179.

15. Zhu S J, et al. Graphene quantum dots with controllable surface oxidation, tunable fluorescence and up-conversion emission. Rsc Advances 2012, 2(7): 2717-2720.

16. Sun H J, Wu L, Gao N, Ren J S, Qu X G. Improvement of Photoluminescence of Graphene Quantum Dots with a Biocompatible Photochemical Reduction Pathway and Its Bioimaging Application. ACS Appl Mater Inter 2013, 5(3): 1174-1179.

17. Liu J J, et al. Glutathione-functionalized graphene quantum dots as selective fluorescent probes for phosphate-containing metabolites. Nanoscale 2013, 5(5): 1810-1815.

18. Tang L, et al. Deep Ultraviolet Photoluminescence of Water-Soluble Self-Passivated Graphene Quantum Dots. ACS nano 2012, 6(6): 5102-5110.

19. Zhang Z P, Zhang J, Chen N, Qu L T. Graphene quantum dots: an emerging material for energy-related applications and beyond. Energy Environ Sci 2012, 5(10): 8869-8890.

20. Yan X, Li B, Li L-s. Colloidal Graphene Quantum Dots with Well-Defined Structures. Acc Chem Res 2012.

21. Zhu S J, et al. Strongly green-photoluminescent graphene quantum dots for bioimaging applications. Chem Commun 2011, 47(24): 6858-6860.

22. Peng J, et al. Graphene Quantum Dots Derived from Carbon Fibers. Nano Lett 2012, 12(2): 844-849.

23. Zhu S J, et al. Surface Chemistry Routes to Modulate the Photoluminescence of Graphene Quantum Dots: From Fluorescence Mechanism to Up-Conversion Bioimaging Applications. Adv Funct Mater 2012, 22(22): 4732-4740.

24. Pan D Y, et al. Cutting sp(2) clusters in graphene sheets into colloidal graphene quantum dots with strong green fluorescence. J Mater Chem 2012, 22(8): 3314-3318.

25. Sun X M, et al. Nano-Graphene Oxide for Cellular Imaging and Drug Delivery. Nano Research 2008, 1(3): 203-212.

26. Dong Y Q, et al. One-step and high yield simultaneous preparation of single- and multi-layer graphene quantum dots from CX-72 carbon black. J Mater Chem 2012, 22(18): 8764-8766.

27. Gao W, Alemany L B, Ci L J, Ajayan P M. New insights into the structure and reduction of graphite oxide. Nat Chem 2009, 1(5): 403-408.

28. Liu Z, Robinson J T, Sun X M, Dai H J. PEGylated nanographene oxide for delivery of water-insoluble cancer drugs. J Am Chem Soc 2008, 130(33): 10876-10877.

29. Cui B X, et al. One at a time, live tracking of NGF axonal transport using quantum dots. Proc Natl Acad Sci USA 2007, 104(34): 13666-13671.

30. Rajan S S, Liu H Y, Vu T Q. Ligand-bound quantum dot probes for studying the molecular scale dynamics of receptor endocytic trafficking in live cells. ACS nano 2008, 2(6): 1153-1166.

31. Saltiel A R, Kahn C R. Insulin signalling and the regulation of glucose and lipid metabolism. Nature 2001, 414(6865): 799-806.

32. Pandini G, et al. Insulin/insulin-like growth factor I hybrid receptors have different biological characteristics depending on the insulin receptor isoform involved. J Biol Chem 2002, 277(42): 39684-39695.

33. Marshall S. Kinetics of insulin-receptor internalization and recycling in adipocytes—shunting of receptors to a degradative pathway by inhibitors of recycling. J Biol Chem 1985, 260(7): 4136-4144.

34. Giudice J, Leskow F C, Arndt-Jovin D J, Jovin T M, Jares-Erijman E. Differential endocytosis and signaling dynamics of insulin receptor variants IR-A and IR-B. J Cell Sci 2012, 125(11): 2786-2786.

35. Trischitta V, Reaven G M. Evidence of a defect in insulin-receptor recycling in adipocytes from older rats. Am J Physiol 1988, 254(1): E39-E44.

36. Hotamisligil G S, et al. IRS-1-mediated inhibition of insulin receptor tyrosine kinase activity in TNF-alpha- and obesity-induced insulin resistance. Science 1996, 271 (5249): 665-668.

37. Inokuchi J. Membrane microdomains and insulin resistance. FEBS Lett 2010, 584(9): 1864-1871.

38. Zou C H, Shao J H. Role of adipocytokines in obesity-associated insulin resistance. J Nutr Biochem 2008, 19(5): 277-286.

39. Zhu S M, et al. Apelin stimulates glucose uptake through the PI3K/Akt pathway and improves insulin resistance in 3T3-L1 adipocytes. Mol Cell Biochem 2011, 353 (1-2): 305-313.

40. Castan-laurell I, Dray C, Knauft C, Kunduzova O, Valet P. Apelin, a promising target for type 2 diabetes treatment? Trends Endocrinol Metab 2012, 23(5): 234-241.

41. Zhang J, Xue R H, Ong W Y, Chen P. Roles of Cholesterol in Vesicle Fusion and Motion. Biophys J 2009, 97(5): 1371-1380.

42. Than A, et al. Apelin inhibits adipogenesis and lipolysis through distinct molecular pathways. Mol Cell Endocrinol 2012, 362(1-2): 227-241.

The invention claimed is:

1. A method to form an insulin-GQD conjugate, wherein a single biomolecule of insulin is coupled to a single graphene quantum dot (GQD), the method comprising:
   contacting a solution containing GQD with 1-ethyl-3-(3-dimethylaminopropyl) carbodiimide hydrochloride (EDC), wherein the GQD comprises one or more carboxyl groups on an edge of the GQD; and wherein 1-ethyl-3-(3-dimethylaminopropyl) carbodiimide hydrochloride reacts with the one or more carboxyl groups to form an O-acylisourea intermediate compound;
   contacting the O-acylisourea intermediate compound with N-hydroxysuccinimide (NHS), to provide an NHS ester-modified GQD; and
   contacting the NHS ester-modified GQD with biomolecules of insulin to form the insulin-GQD conjugate, wherein the insulin-GQD conjugate is suitable for imaging an interior of a living cell.

2. The method of claim 1, further comprising contacting the insulin-GQD conjugate with hydroxylamine solution.

3. A fluorophore comprising an insulin-GQD conjugate, wherein a single biomolecule of insulin is coupled to a single GQD, obtained by a method comprising:
   contacting a solution containing GQD with 1-ethyl-3-(3-dimethylaminopropyl) carbodiimide hydrochloride (EDC), wherein the 1-ethyl-3-(3-dimethylaminopropyl) carbodiimide hydrochloride reacts with one or more carboxyl groups present on an edge of the GQD to form an O-acylisourea intermediate compound;
   contacting the O-acylisourea intermediate compound with N-hydroxysuccinimide (NHS), wherein the O-acylisourea intermediate compound reacts with the N-hydroxysuccinimide (NHS) to form a NHS ester-modified GQD; and
   contacting the NHS ester-modified GQD with biomolecules of insulin to form the insulin-GQD conjugate, wherein the insulin-GQD conjugate is suitable for imaging an interior of a living cell.

4. An imaging method, comprising:
   administering a fluorophore to a subject, wherein the fluorophore comprises an insulin-GQD conjugate, wherein a single biomolecule of insulin is coupled to a single GQD, obtained by a method comprising:
   contacting a solution containing GQD with 1-ethyl-3-(3-dimethylaminopropyl) carbodiimide hydrochloride (EDC), wherein the 1-ethyl-3-(3-dimethylaminopropyl) carbodiimide hydrochloride reacts with one or more carboxyl groups present on an edge of the GQD to form an O-acylisourea intermediate compound;
   contacting the O-acylisourea intermediate compound with N-hydroxysuccinimide (NHS), wherein the O-acylisourea intermediate compound reacts with the N-hydroxysuccinimide (NHS) to form a NHS ester-modified GQD; and
   contacting the NHS ester-modified GQD with biomolecules of insulin to form the insulin-GQD conjugate, wherein the insulin-GQD conjugate is suitable for imaging an interior of a living cell; and
   collecting imaging data of the subject or part of the subject with an optical imaging.

5. The imaging method of claim 4, wherein the optical imaging comprises optical multimodality imaging.

6. The imaging method of claim 4, wherein the optical imaging is ex vivo imaging.

7. The imaging method of claim 4, wherein the optical imaging is confocal fluorescence imaging.

8. The imaging method of claim 4, wherein the subject is a mammal.

9. The imaging method of claim 7, wherein the part of the subject is a mammalian adipocyte cell.

10. The method of claim 1 wherein forming the NHS ester-modified GQD comprises coupling NHS to the one or more carboxyl groups by ester bonds.

11. The method of claim 1 wherein forming the insulin-GQD conjugate comprises forming an amide bond between an amine of the biomolecule of insulin and a carboxyl group of GQD.

\* \* \* \* \*